United States Patent [19]

Verma

[11] 4,296,205
[45] Oct. 20, 1981

[54] CELL CULTURE AND CONTINUOUS DIALYSIS FLASK AND METHOD

[76] Inventor: Dharmvir S. Verma, 5831 Rutherglen, Houston, Tex. 77096

[21] Appl. No.: 123,552

[22] Filed: Feb. 22, 1980

[51] Int. Cl.³ .......................... C12M 3/04; C12N 5/00
[52] U.S. Cl. .................................. 435/240; 435/285; 435/296; 435/310; 210/644
[58] Field of Search ............... 435/240, 285, 241, 296, 435/310, 284; 210/637, 634, 644, 645

[56] References Cited
U.S. PATENT DOCUMENTS
3,275,528  9/1966  Ainis ............................. 435/240 X OTHER PUBLICATIONS
Dexter, *Clinics in Haematology*, 8(2), (1979), 453–467.
Marbrook et al., *The Lancet*, 2 (1967), 1279–1281.
Feldman et al., *J. Exp. Med.*, 136, (1972), 49–67.

*Primary Examiner*—Esther M. Kepplinger
*Attorney, Agent, or Firm*—Arnold, White & Durkee

[57] ABSTRACT

An apparatus and method for culturing tissue or cells and for the preparation of conditioned culture media is disclosed. More particularly, the apparatus and method applies continuous simultaneous dialysis of the culture media. The apparatus and method are particularly applicable to the long term growth in vitro of cell populations and the preparation of associated conditioned culture media.

12 Claims, 3 Drawing Figures

CELL CULTURE AND CONTINUOUS DIALYSIS FLASK AND METHOD

BACKGROUND OF THE INVENTION

1. Field of the Invention

The invention relates to a flask used in the culturing of cells or tissue. The flask may be used in the preparation of cultured cells or of conditioned media from the cells. More particularly, a flask and method providing for continuous dialysis of the culture media is disclosed. The flask and method are particularly useful for the preparation of conditioned media from tissues or various cell populations or for the long term in vitro growth and maintenance of cells.

2. Description of the Prior Art

The need exists for methods of preparing quantities of conditioned media from tissues or various cell populations. The preparation of conditioned media is a routine procedure in tissue culture and hemopoiesis laboratories which are involved in investigating various cell-cell interactions and other regulatory phenomena. Long term in vitro growth and maintenance of cells is also of interest in these laboratories.

The prior art preparation of conditioned media is a multi-step process. First, the conditioned media is prepared in a Petri dish or a simple tissue culture flask, such as a flat stoppered tissue culture flask. After preparation, the media is harvested and dialyzed. The dialysis step removes putative low molecular weight inhibitors of cell growth. This multi-step process involves considerable manipulation of the conditioned media, resulting in the loss of some quantities of the media. This loss may be significant when rather small quantities of conditioned media are prepared. More importantly, this manipulation may result in some heretofore unanticipated inadvertent changes in the qualities of the conditioned media.

The prior art methods of growing long term in vitro cell cultures generally include the use of flat tissue culture flasks. Cells are introduced into the flasks in a suspension in the culture media supplemented with horse serum and other nutrients. The flat tissue culture flasks are then incubated lying on their flat sides. A part of the culture media is withdrawn and replaced with fresh media at frequent intervals. Often half of the media is replaced twice a week. This preparation method is known as the "Dexter Method". See Dexter, T. M., "Cell Interactions in vitro", Clinics in Haematology 8, 453-468 (1979), at 454-455 for a specific example of the "Dexter Method." Although the "Dexter Method" is able to maintain mouse haemopoietic stem cells for as many as twelve to sixteen weeks, it is unable to maintain human stem cells beyond a period of four to five weeks.

Disadvantages of the "Dexter Method" include the accumulation of putative inhibitory molecules in the culture media necessitating frequent replacement of a portion of the culture media. Another disadvantage associated with the frequent replacement of the culture media is the removal of stimulatory macromolecules essential for the maintenance and growth of the required cells. These factors may be responsible for the inability to maintain long term growth of the cultures.

A prior art method providing for continuous dialysis is the "Marbrook System" and its modifications. See Marbrook, J., "Primary Immune Response in Cultures of Spleen Cells," The Lancet 2, 1279-1281 (1967), at 1280; Feldmann, M., and A. Basten, "Cell Interactions in the Immune Response in Vitro III. Specific Collaboration Across a Cell Impermeable Membrane," J. Exp. Med. 136, 49-67 (1972), at 51. The Marbrook System is often used for investigating the effects of humoral factors elaborated by one cell population over another. The Marbrook System employs a flask similar to an Erlenmeyer flask to contain the dialysate solution. An inner chamber with a dialysis or millipore membrane sealed to the open end contains the culture media and cells. This inner chamber is partially submerged in the dialysis solution of the outer chamber. The cells to be cultured are placed directly on the dialysis membrane.

Disadvantages of the "Marbrook System" include the inability to maintain and establish long-term tissue cultures. Other disadvantages are the problems associated with the clogging of the dialysis membrane caused by placing the cells to be cultured directly on the membrane. Still other problems are associated with the microenvironment on the dialysis membrane.

Accordingly, prior to the development of the present invention, there has been no cell culture and continuous dialysis flask and method which solves the problems and overcomes the disadvantages associated with the prior art flasks and methods discussed above. The flask and method described by the present invention is able to culture cells or tissue over long periods of time while simultaneously dialyzing the conditioned culture media under preparation. This results in a significant saving of time and in a minimization of manipulation of the media. This minimization of manipulation results in less contamination, change and loss of the media. The flask and method described by the present invention does not require frequent replacement of the culture media. Thus putative inhibitory molecules in the culture media are removed by continuous simultaneous dialysis while stimulatory macromolecules remain unaffected. The flask and method described by the present invention provides a tissue culture shelf for the establishment of a "feeder layer" of the cells to be cultured. This shelf helps to prevent the clogging of the dialysis membrane and the problems associated therewith.

The art has long sought a tissue culture flask and method which could be used to prepare conditioned media or to grow cells for long terms in vitro by providing continuous simultaneous dialysis of the culture media. As shown below, the flask and method of the present invention meets this need.

SUMMARY OF THE INVENTION

The flask and method of the present invention, which involves continuous dialysis of the culture media, overcomes many of the foregoing disadvantages and achieves the foregoing benefits.

The present invention provides a flask and method for the preparation of conditioned media from tissues or various cell populations and for long term in vitro growth and maintenance of cells.

The flask of the present invention comprises two chambers separated by a dialysis, nuclepore or millipore membrane. The upper chamber is known as a tissue culture chamber. The lower chamber is the dialysis chamber. The upper chamber further comprises two compartments, formed by a tissue culture shelf. The upper compartment is known as the tissue culture compartment. The lower compartment is a dialysis compartment. The shelf separating the compartments has one or more perforations.

The tissue culture chamber should be constructed of a transparent or translucent material of a tissue culture grade which is nontoxic to living cells. Examples of suitable materials include glass, lucite and plexiglass. At least the tissue culture compartment must be constructed of transparent material to permit the growth of cells or tissue and the observation and manipulation of the cultured cells by the user.

A feature of the invention is the tissue culture shelf, providing a compatible surface for the establishment of a "feeder layer" of cells. This "feeder layer" is essential for the long-term maintenance of haemopoietic stem cells. This tissue culture shelf should have one or more perforations. The perforations permit the addition of culture media to the dialysis compartment below the tissue culture shelf. As the level of media rises, it passes through the perforations and slowly covers the tissue culture shelf and any cells or tissue deposited thereon without disturbing said cells or tissue. The perforations also provide for the downward passage of low molecular factors toward the dialysis, nuceopore or millipore membrane where they are diffused out of the culture media. The edges of the tissue culture shelf surrounding these perforations may be upraised so that the shelf itself forms tray-like areas on which the cells or tissue will grow.

Another feature of the invention is an opening near the top of the tissue culture chamber. This opening provides access to the chamber. Tissue or cells may be placed upon and withdrawn from the tissue culture shelf through this opening. The culture media may also be placed into or withdrawn from the chamber through this opening.

Features of the dialysis chamber include filling and draining mechanisms. These permit the draining of contaminated dialysate and the addition of fresh dialysate in long term growth cultures without disturbance of the cultured cells or tissue.

Another feature of the flask is a replaceable dialysis, nuceopore or millipore membrane. This feature would increase the versatility of the flask, by permitting many different membranes to be used with the same tissue culture/dialysis flask.

Another feature of the invention is the separability of the tissue culture chamber from the dialysis chamber. In this way many sizes and shapes of dialysis chambers may be used with any given tissue culture chamber, increasing the versatility of the flask to meet varied needs of the researcher.

In general the dialysis chamber should be of a substantially larger volume, e.g. about 50 times greater, than the volume of the tray-like areas of the tissue culture shelf to permit operation for longer periods of time without the need to change the dialysate solution.

The method of culturing cells or preparing conditioned media comprises the steps of the culturing of cells on the tissue culture shelf of the tissue culture chamber, the simultaneous dialysis of the culture media through the dialysis, nucleopore or millipore membrane separating the dialysis compartment of the tissue culture chamber from the dialysis chamber, and the withdrawal of the desired cultured cells or conditioned culture media from the tissue culture chamber. The method further includes the steps of placing the cells or tissue on the perforated tissue culture shelf, filling the dialysis compartment with the culture media until it overflows through the perforations of the tissue culture shelf and covers the cells or tissue, and filling the dialysis chamber with a dialysate solution as necessary.

The flask and method of the present invention, when compared with previously proposed prior art flasks and methods, has the advantages of permitting the long term growth of cells in vitro and the preparation of conditioned culture media. These advantages are achieved by the provision of a shelf for the establishment of a "feeder layer" of cells and the continuous dialysis of the culture media. Manipulation of the cells and media is reduced, thus, decreasing contamination, change and loss of cells or media. A significant saving of time, as much as several days, in the preparation of conditioned media is achieved by the elimination of the additional time spent in dialyzing the media after it has been prepared and harvested. The flask of the present invention offers great versatility in the ability to interchange tissue culture chambers, dialysis chambers, and dialysis, nucleopore or millipore membranes to meet the varied needs of the user.

While the invention will be described in connection with the preferred embodiment, it will be understood that it is not intended to limit the invention to that embodiment. On the contrary, it is intended to cover all alternatives, modifications, and equivalents as may be included within the spirit and scope of the invention as defined by the appended claims.

DETAILED DESCRIPTION OF THE PREFERRED EMBODIMENT

Figure 1:
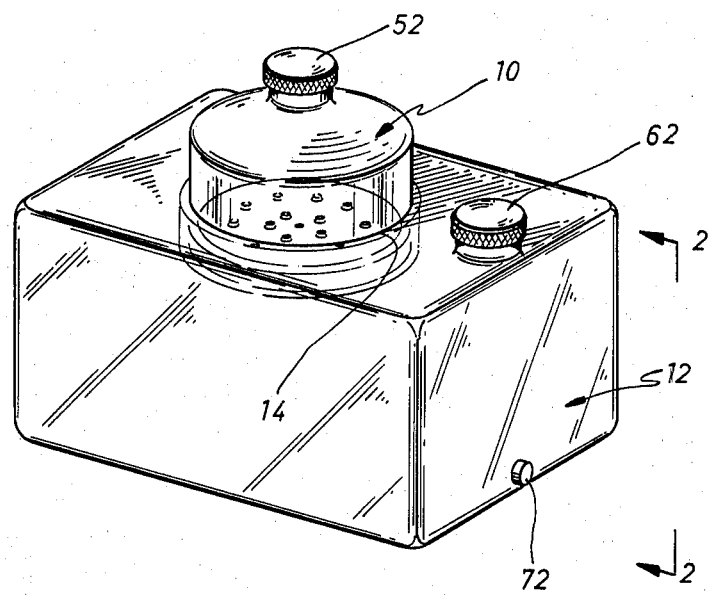
FIG. 1 is a perspective drawing of the flask of the present invention.

FIG. 1 illustrates one embodiment of the invention. The flask of the present invention is shown to comprise a tissue culture chamber 10, a dialysis chamber 12, and a dialysis, nucleopore or millipore membrane 40 separating chambers 10 and 12. There is no restriction on the size or shape of the tissue culture chamber 10 or the dialysis chamber 12. However, it is recommended that the volume of chamber 12 be substantially greater than the volume of the tray area 36 of tissue culture shelf 30. Preferably the volume of chamber 12 is at least 50 times greater than the volume of the tray area 36 of tissue culture chamber 10, in order to minimize the necessity of changing the dialysate solution present in dialysis chamber 12, as will be hereinafter discussed. The tissue culture chamber 10 is preferably constructed of a tissue culture grade material such as glass, lucite or plexiglass which is nontoxic to the cultured cells; however, any other material which is nontoxic to the cultured cells may be used. At least a portion of chamber 10 should preferably be transparent to permit the growth of cells and to permit the user to observe and manipulate the cultured cells. The dialysis chamber 12 may be constructed of any suitable material and may even be disposable.

Figure 2:
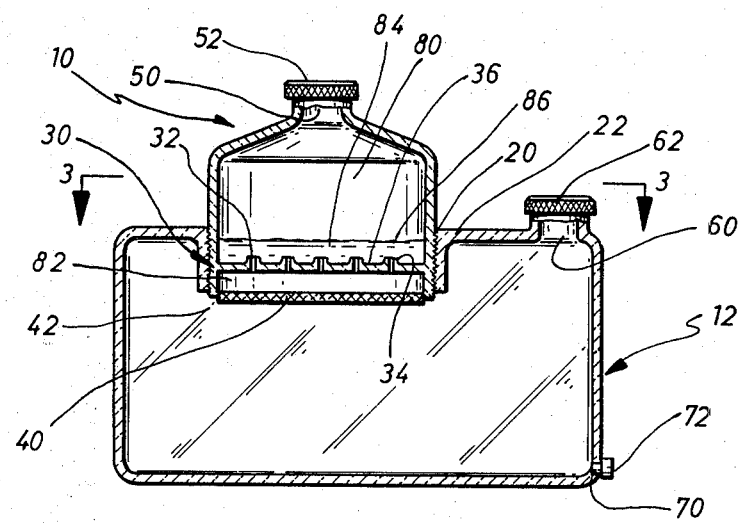
FIG. 2 is a cross-sectional drawing of the flask of the present invention taken along lines 2—2 of FIG. 1.
Figure 3:
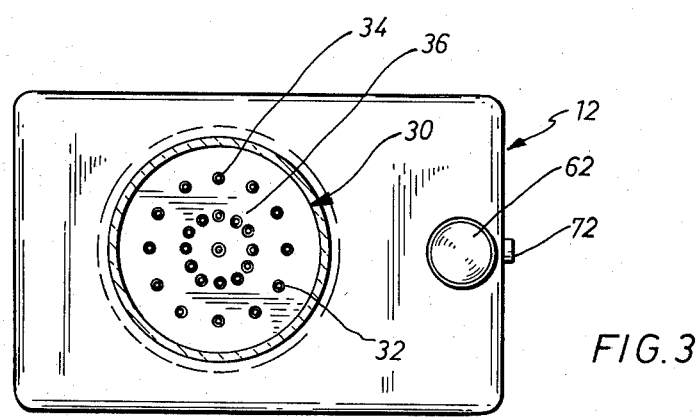
FIG. 3 is a cross-sectional drawing of the tissue culture chamber taken along lines 3—3 of FIG. 2.

As shown in FIG. 2, the tissue culture chamber 10 is divided by a tissue culture shelf 30 into an upper tissue culture compartment 80 and a lower dialysis compartment 82. The tissue culture shelf 30 is characterized by one or more perforations 32. The edges 34 of these perforations are upraised forming tray-like areas 36 on the tissue culture shelf 30. The tissue or cells to be cultured (not shown) may be placed upon the tray-like areas 36.

An opening 50 in the tissue culture chamber 10 permits access thereto so that cells or tissue to be cultured may be placed on trays 36 through opening 50 using pipets, syringes or other similar instruments. The culture media may also be placed in chamber 10 by inserting a pipet, syringe or other instrument through opening 50 and through one of the perforations 32, and discharging culture media in compartment 82 below shelf 30. A lid, stopper or cap, 52 or other suitable closing means may be employed to close opening 50.

Still referring to FIGS. 1 and 2, it is seen that a drainage orifice 70 or other mechanism may be provided in dialysis chamber 12. Similarly, a filling orifice 60 or other mechanism may be provided in dialysis chamber 12. These orifices 60 and 70 permit the changing of dialysate solution in chamber 12 during the culturing of cells or media without disturbing the cells or media in tissue culture chamber 10. A simple drainage system includes an orifice 70 and lid, stopper or cap 72. The cap 72 may threadably engage the orifice 70. Similarly, filling orifice 60 may be equipped with a lid, stopper or cap 62, which may also threadably engage the orifice 60.

A dialysis, nucleopore or millipore membrane 40 separates the tissue culture chamber 10 from the dialysis chamber 12. This membrane may be of any suitable porosity. It may also be replaceable. In one embodiment of the invention, the tissue culture chamber 10 is threadably inserted into the top of the dialysis chamber 12 as shown in FIG. 2. The tissue culture chamber 10 may be removed and the membrane 40 replaced. Membrane 40 may be threadably or slidably attached to tissue culture chamber 10. Membrane 40 may also be held attached to tissue culture chamber 10 by use of an O-ring or other similar attaching means. This embodiment of the invention also permits the use of dialysis chambers 12 of various sizes and shapes to accommodate different usages in connection with tissue culture chamber 10.

In the method of culturing cells or preparing conditioned media of the present invention, the cells (not shown) are placed on tray-like areas 36 by use of a pipet, syringe or other mechanism inserted through opening 50 in tissue culture chamber 10. A pipet, syringe or other mechanism is used to discharge a tissue culture media 84 into dialysis compartment 82 by inserting said mechanism through opening 50, through one of the perforations 32 and by discharging said fluid in compartment 82 until said compartment is filled to overflowing as shown at 86. The fluid rises through perforations 32 into tissue culture compartment 80 and covers the tissue or cells deposited on tray-like areas 36 to fluid level 86. Dialysis chamber 12 is filled with a dialysate solution through filling orifice 60. In operation, the cells or tissue may be cultured over long periods of time without disturbance. The tissue culture media is continuously dialyzed through dialysis, nucleopore or millipore membrane 40. Dialysis chamber 12 is generally of a volume much larger, e.g. 50 times larger, than the volume of the tray-like areas 36 of the tissue culture shelf 30 of the tissue culture chamber 10. This generally eliminates the need to change the dialysate solution. However, if it becomes necessary to change the dialysate solution during the course of long-term cell culturing, the solution may be changed without affecting the culturing by draining through orifice 70 and refilling through orifice 60. The cultured tissue or conditioned tissue media may be withdrawn from chamber 10 through opening 50 by using a pipet, syringe or other suitable mechanism.

The foregoing description of the invention has been directed in primary part to a particular preferred embodiment in accordance with the requirements of the Patent Statutes and for purposes of explanation and illustration. It will be apparent, however, to those skilled in the art that many modifications and changes in this specific apparatus may be made without departing from the scope and spirit of the invention. For example, many sizes and shapes of dialysis chambers and tissue culture chambers may be combined to form flasks for particular culturing problems.

It is applicant's intention in the following claims to cover such modifications and variations as fall within the true spirit and scope of the invention.

What is claimed is:

1. In a flask for the growth of cells or the preparation of conditioned media comprising a tissue culture chamber, a dialysis chamber and a dialysis or millipore membrane separating said chambers, the improvement comprising a tissue culture shelf separating the tissue culture chamber into a tissue culture compartment and a dialysis compartment, said shelf having one or more perforations, wherein the edges of said tissue culture shelf surrounding said perforations are upraised to form tray-like areas so that cells cultured on said shelf do not pass over said edges and through said perforations.

2. A flask for the growth of cells or the preparation of conditioned media from cells, comprising:
   (a) a tissue culture chamber including:
      (1) an upper tissue culture compartment to contain the cells or tissue to be cultured and the culture media;
      (2) a lower dialysis compartment to also contain the culture media; and
      (3) a tissue culture shelf separating said compartments and forming a tray-like area, said shelf having one or more perforations, wherein the edges of said tissue culture shelf surrounding said perforations are upraised to form tray-like areas so that cells cultured on said shelf do not pass over said edges and through said perforations;
   (b) a dialysis chamber to contain a dialysate solution; and
   (c) a dialysis, nucleopore or millipore membrane separating said chambers to permit the continuous dialysis of the culture media.

3. The flask as described in claim 2, wherein said tissue culture chamber is constructed of a transparent or translucent material of a tissue-culture grade which is nontoxic to living cells.

4. The flask as described in claim 2, wherein said tissue culture chamber further comprises an opening near the top thereof permitting access to said tissue culture shelf.

5. The flask as described in claim 2, wherein said dialysis chamber further comprises:
   (a) a drainage mechanism located at the lower part of said chamber; and
   (b) a filling mechanism located in said chamber at a point higher than said tissue culture shelf.

6. The flask as described in claim 2, wherein said dialysis, nucleopore or millipore membrane is replaceable.

7. The flask as described in claim 2, wherein said tissue culture chamber is separable from said dialysis chamber.

8. The flask as described in claim 2, wherein the volume capacity of said dialysis chamber is substantially greater than the volume capacity of said tray-like areas of said tissue culture shelf.

9. The flask as described in claim 8, wherein the volume capacity of said dialysis chamber is at least about 50 times greater than the volume capacity of said tray-like areas of said tissue culture shelf.

10. A method of culturing cells or preparing conditioned media from cells comprising the steps of:
   (a) culturing cells or preparing culture media in a tissue culture chamber on a tissue culture shelf, said shelf having one or more perforations, wherein the edges of said tissue culture shelf surrounding said perforations are upraised to form tray-like areas so that cells cultured on said shelf do not pass over said edges and through said perforations
   (b) dialyzing the culture media simultaneously with a dialysate solution contained in a dialyzing chamber separated from said tissue culture chamber by a dialysis or millipore membrane; and
   (c) withdrawing the desired cultured cells or culture media from the tissue culture chamber.

11. The method as recited in claim 10, wherein the culturing or preparing step includes the steps of:
   (a) placing cells or tissue on a perforated tissue culture shelf which separates a tissue culture compartment from a dialysis compartment;
   (b) filling said dialysis compartment with a culture media; and
   (c) overflowing said culture media through the perforations of said tissue culture shelf, partially filling said tissue culture compartment and covering said cells or tissue.

12. The method as recited in claim 11, wherein the dialyzing step comprises:
   (a) filling said dialyzing chamber with a dialysate solution;
   (b) draining said dialysate solution and refilling said dialyzing chamber at intervals sufficient to maintain proper growth of the tissue.

* * * * *